United States Patent [19]

Huddleston

[11] Patent Number: 4,877,894

[45] Date of Patent: Oct. 31, 1989

[54] HYDROCARBON GELLER AND METHOD FOR MAKING THE SAME

[75] Inventor: David A. Huddleston, Sugar Land, Tex.

[73] Assignee: Nalco Chemical Company, Sugar Land, Tex.

[21] Appl. No.: 142,703

[22] Filed: Jan. 11, 1988

[51] Int. Cl.[4] .................................................. C07F 9/00
[52] U.S. Cl. .................................... 558/113; 558/208; 252/8.551
[58] Field of Search ................................ 558/113, 208

[56] References Cited

FOREIGN PATENT DOCUMENTS 225661 6/1987 European Pat. Off. .

*Primary Examiner*—Anton H. Sutto
*Attorney, Agent, or Firm*—Vinson & Elkins

[57] ABSTRACT

An improved hydrocarbon gelling agent is disclosed comprising the reaction product of (1) a polyphosphate intermediate produced by reacting triethyl phosphate and phosphorous pentoxide and (2) a mixed alcohol having a substantial hexanol component, together with methods of making and using such gelling agent.

6 Claims, No Drawings

HYDROCARBON GELLER AND METHOD FOR MAKING THE SAME

BACKGROUND OF THE INVENTION

This invention relates to an improvement in making gelled hydrocarbons, especially those used in hydraulic fracturing of subterranean formations to enhance oil and gas production.

Hydraulic fracturing is a widely used method for stimulating oil and/or gas production. In performing a fracturing operation, a hydraulic fluid, usually a liquid hydrocarbon, is pumped into the well bore at sufficiently high pressure to fracture the surrounding rock formation to open cracks in the formation through which oil and/or gas can flow into the well bore. Since the cracks which are opened by the fracturing fluid tend to close once the pressure on the fluid is released, it is customary to inject into the well along with the fracturing fluid a suitable particulate proppant material such as sand. The small proppant particles flow into the fractures created in the formation along with the fracturing fluid and serve to prop the fractures open after the fluid pressure is released.

Proppant materials may be either lighter or heavier than the hydraulic fracturing fluid and thus may tend to float or settle out of the fluid prematurely, or otherwise be unevenly distributed in the fracturing fluid. To overcome this problem, it is customary practice to use gelled fracturing fluids which will hold the proppant material in suspension as the fluid flows down the well bore and out into the formation fractures. This requires that the gelled fracturing fluid be of sufficient viscosity to hold the proppant material suspended in a slurry or matrix. At the same time, the fluid must not be so viscous that it cannot be readily pumped into the well bore and out into the formation fractures.

Various materials are known which, when admixed with hydrocarbons, will create hydrocarbon gels of various viscosities. However, many of these materials are not suitable for use as hydrocarbon fracturing fluids because of the particular requirements imposed by the environment in which they are used. The gels must be formed at or near the wellhead at ambient temperature. Generally, several thousand gallons of normally liquid hydrocarbon such as crude or refined oil, a gelling agent and an activator are blended to form a gel. This mixture then is stored in frac tanks until used. Due to various factors such as the amount of fracturing fluid needed, labor schedules and other outside influences, the gel may be used promptly or a substantial period of time may elapse between the time the gel is initially formed and the time it is used. Therefore, it is desirable that the gel thicken relatively quickly to a sufficient viscosity to suspend the proppant material, but at the same time have stability over as long a period of time as possible so that it neither breaks down into a less viscous fluid, nor sets into a gel of such high viscosity that it cannot be pumped into the formation, before it is used.

Additional complications are presented by the fact that, while the gel is formed at ambient temperature at the wellhead, it is utilized in deep formations where temperatures may be much higher. Depending upon the depth, formation temperatures may be in the range of 200° to 250° Fahrenheit or higher. Such elevated temperatures tend to reduce the viscosity of the gelled liquid. Prior art gelled hydrocarbons which are of sufficient viscosity to suspend the proppant, but not too viscous to pump, generally will not retain sufficient viscosity at temperatures of 200° to 250° or more to retain the proppant in suspension.

An ideal gelling agent for forming a gelled hydrocarbon fracturing fluid would be one which, when mixed with the normally liquid hydrocarbon and an activator, relatively quickly forms a gel of sufficient viscosity to hold the proppant in suspension and then retains its desired range of viscosity for at least several hours at ambient temperatures. At the same time, the gel should, when injected into downhole formations at temperatures of 200° to 250°, retain sufficient viscosity to keep the proppant in suspension for the period of time required for the fracturing operation, which may be up to eight hours. It is accordingly the primary object of the rresent invention to provide an improved gelling agent, hydrocarbon gel, and methods of making and using the same, which meet these criteria.

DESCRIPTION OF THE PRIOR ART

Various gelling agents and methods are shown in the prior art for producing hydrocarbon gels. See, for example, the following U.S. Pats:

| | |
|---|---|
| 2,983,678 | 4,104,173 |
| 2,983,679 | 4,152,289 |
| 3,334,978 | 4,153,649 |
| 3,338,935 | 4,174,283 |
| 3,494,949 | 4,200,539 |
| 3,505,374 | 4,200,540 |
| 3,575,859 | 4,316,810 |
| 3,757,864 | 4,537,500 |
| 4,003,393 | |

None of these, however, discloses a hydrocarbon gel which will possess sufficient viscosity at ambient temperatures to retain the proppant in suspension, sufficient shelf life at ambient temperatures to permit the gel to be retained at the well site for at least several hours prior to use, and sufficient viscosity at elevated subterranean temperatures of up to 250° to retain the proppant in suspension during the fracturing operations.

Unable to meet these goals with a single gel, the prior art has utilized a two-step method in which a first gel is formed which is stable at surface temperatures and to which additional geller or activator is added as the gel is pumped into the well to increase its viscosity at elevated downhole temperatures. See, for example, U.S. Pat. Nos. 4,200,540 and 4,622,155 assigned to Halliburton Company. This two step procedure has significant drawbacks. Adding additional gelling agent or activator "on the fly" as the gel is being pumped into the well makes it difficult to assure proper measurement and mixing of the additional ingredients. Further, if the additional gelling agent or activator acts too quickly, it can cause the viscosity of the gel to increase too quickly, thus making it nonpumpable. If the additional agent acts too slowly, the gel may reach the elevated temperature zone without developing sufficient additional viscosity. The gel viscosity can then drop, permitting the proppant to fall out of suspension. Obviously, it would be far preferable to provide a single initial gel mixture possessing the desired surface and the desired downhole viscosities at both ambient surface temperature and elevated downhole temperature.

Nalco Chemical Company, assignee of the present application, previously has produced a hydrocarbon geller under the designation "ASP-160." This product is an alkyl phosphate acid prepared by reacting approximately three moles of mixed aliphatic alcohols having carbon numbers 6 to 10 and comprising approximately 4% $C_6$ alcohol, 53% $C_8$ alcohol and 43% $C_{10}$ alcohol by weight per mole of phosphorous pentoxide to produce a phosphate intermediate and then reacting the intermediate with triethylphosphate. The resulting alkyl phosphate ester is then blended with normally liquid hydrocarbon at the rate of approximately 6 gallons per thousand gallons of hydrocarbon and crosslinked with a sodium aluminate activator to produce a hydrocarbon gel. This gel exhibits satisfactory characteristics at wellhead ambient temperatures, but tends to lose viscosity rapidly at downhole temperatures exceeding 225° Fahrenheit.

DESCRIPTION OF THE PREFERRED EMBODIMENT

The improved hydrocarbon gelling agent or geller according to the present invention comprises the reaction product of (1) a polyphosphate intermediate produced by reacting triethyl phosphate and phosphorous pentoxide and (2) a mixed aliphatic alcohol in which hexanol is a substantial constituent. Its ingredients are qualitatively the same as those of ASP-160, but the proportion of hexanol used is substantially increased, resulting unexpectedly in significant improvement in high temperature viscosity of the gel, while maintaining a pumpable viscosity at ambient temperatures.

In producing the polyphosphate intermediate, it is preferred to use from about 1.0 to about 1.3 moles of triethyl phosphate for each mole of phosphorous pentoxide, with 1.3 moles of triethyl phosphate being most preferred. Approximately three moles of mixed aliphatic alcohols for each mole of phosphorous pentoxide used are then blended with the polyphosphate intermediate.

The alcohol comprises a mixture of aliphatic alcohols having from 6 to 10 carbons in their alkyl groups. Importantly, it has been discovered in accordance with the present invention that by substantially increasing the hexanol component of the mixed alcohol, the gelling agent is capable of producing a gel having a much higher viscosity at elevated temperatures in the range of 200° to 250° F., while retaining acceptable viscosity at ambient temperatures below 100° F. Accordingly, the mixed alcohol has an increased hexanol content of from about 13% to about 92% by weight of hexanol, with the remainder being divided principally between $C_8$ and $C_{10}$ alcohols. Most preferably, the mixed alcohol comprises approximately 23% by weight of hexanol, 42% by weight of octanol and 35% by weight of decanol.

An improved hydrocarbon gel may be produced utilizing the gelling agent of the present invention by blending with a normally liquid hydrocarbon a gelling amount of the gelling agent and an effective amount of an alkaline aluminate activator. Typically normally liquid medium density petroleum fractions such as kerosene, gas oil, crude oil, or diesel are used. From about 6 to about 10 gallons of the gelling agent preferably are utilized for each 1,000 gallons of hydrocarbon, with approximately 6 gallons of gelling agent per 1,000 gallons of hydrocarbon being most preferred. Of the alkaline metal aluminate activators, sodium aluminate is preferred. Most preferably, an aqueous solution of sodium aluminate is utilized.

A gelled hydrocarbon produced in accordance with the present invention will set quickly at ambient temperatures in the range of 40° F. to 100° F. to produce a gel having a viscosity in the range of approximately 40 to 80 centipoise, which is well within the pumpable viscosity range and is satisfactory for suspension of most or all normal proppants. The gel is stable in that viscosity range for 48 hours or longer. Further, the gel demonstrates a stable viscosity in the temperature range of 250° F. of approximately 100 to 200 centipoise, which is sufficient for retaining most or all well proppants in suspension.

When using the improved gelling agent to perform a well fracturing operation, the gelling agent, liquid hydrocarbon and activator are blended in one or more frac tanks at or near the well site. The frac tanks may be up to several thousand gallons each and from one to four or more frac tanks may be utilized depending upon the size of the fracturing operation. Commonly, the frac tanks are filled in series so that up to several hours may elapse between the time the hydrocarbon gel is formed in the first frac tank and the time it is formed in the last frac tank. Once the fracturing operation is begun, the gelled hydrocarbon is pumped from the frac tanks, mixed with the proppant and pumped down the well bore at the desired formation fracturing pressure and out into the formation fractures. The target formation may be kept under elevated pressure for up to several hours to promote further propagation of cracks. Therefore, it is desirable that the gelled hydrocarbon viscosity remain stable in the temperature range of 200 to 300°F. for several hours.

Once the fracturing operation is complete, the pressure on the hydraulic fracturing fluid is released. However, gelled hydrocarbon trapped in the fractures might tend to prevent production flow from the fractured formation back into the well bore. To avoid this, a neutralizing or "breaking" agent commonly is admixed with the gelled hydrocarbon as it is pumped into the well bore. The preferred breakers have a delayed neutralizing effect and thus tend to break down the hydrocarbon gel only after several hours. One suitable such breaking agent is sodium bicarbonate which may be admixed with the hydrocarbon gel in a finely granulated or powder form. It has only low solubility in the gelled hydrocarbon and therefore its neutralizing effect is suitably time delayed.

The following examples and experimental results will further illustrate the invention.

EXPERIMENTAL

Funnel Times

In the following examples a funnel flow test was used to approximate the gelled viscosities at low shear rates, characteristic of a pumpable gel. In the procedure, a Baroid Marsh funnel is filled with 200 ml. of the sample gelled hydrocarbon. An electronic balance with a plastic collection cup is placed below the funnel. A measurement is taken of the time required to flow 100 grams of the gelled hydrocarbon into the cup, usually recorded as seconds per 100 grams. Generally a funnel time of 200 seconds or less per 100 grams is considered a pumpable viscosity.

EXAMPLE 1

A 4-neck reaction flask was used, equipped with a thermometer, mechanical stirrer, condenser and gas (N$_2$) inlet. Triethyl phosphate (TEP) and phosphorous pentoxide (P$_2$O$_5$) were mixed in a mole ratio of 1.32 moles of TEP to 1.0 moles of P$_2$O$_5$ and reacted for two hours at 175° F. to produce a polyphosphate intermediate All additions and reactions throughout the experiment were conducted under a nitrogen blanket.

The reaction was exothermic and was complete after two hours at 175° F. The temperature then was allowed to drop back to 140° F. A mixture of fatty C$_6$ to C$_{10}$ lineasr alcohols comprising approximately 23 weight percent hexanol, 42 weight percent octanol and 35 weight percent decanol was than added to the polyphosphate intermediate while holding the temperature at 140° to 175° F. The fatty alochol mixture was added dropwise to the polyphosphate intermediate. Three moles of the fatty alcohol mixture was used for each mole of phosphorous pentoxide used in producing the intermediate. After completing the fatty alcohol addition, the temperature was allowed to increase to 250° F. to 260° F. and held there for two hours to complete the reaction. The reaction product was the geller in liquid form, an alkyl phosphate diester easily poured from the flask.

The liquid geller was readily soluble in a paraffinic hydrocarbon oil. The geller was mixed with kerosene in a Waring blender at a volume ratio equivalent to six gallons of geller per 1,000 gallons of kerosene (a "6 gpt" ratio"). A sodium aluminate activator (comprising approximately 32 weight percent sodium aluminate, 7 weight percent sodium hydroxide and 61 weight percent water) was added dropwise in an effective amount to form the gelled hydrocarbon. It is believed that the gelling viscosity is imparted to the hydrocarbon by the formation of an alumino alkyl phosphate ester as the reaction product between the sodium aluminate activator and the alkyl phosphate diester.

After aging approximately twenty-four hours at 75° F., the resulting gelled hydrocarbon was found to have a funnel time of 128 seconds, representing a viscosity of 50 centipoise at 170 reciprocal seconds shear rate. At a temperature of 250° F., the gelled hydrocarbon had a viscosity of 140 centipoise and was stable at such viscosity range and temperature for three hours.

EXAMPLE 2

The procedure of Example 1 was followed except that the geller to kerosene concentration was at a ratio equivalent to 10 gallons of geller per thousand gallons of kerosene ("10 gpt").

The resulting gel after aging for twenty-four hours at 75° F. had a funnel time of 124 seconds and a viscosity of 78 centipoise measured at 170 reciprocal seconds shear rate. When heated to 275° F., the gel had a viscosity of 179 centipoise. The viscosity declined 7% over a period of three hours at 275° F.

EXAMPLE 3

The procedure of example 1 was followed with the following changes:

(1) the mole ratio of triethylene phosphate to phosphorous pentoxide was 1.0 to 1.0; and (2) the mixed fatty alcohol comprised approximately 84 weight percent hexanol, 8.5 weight percent octanol and 7.5 weight percent decanol.

After standing for three days, the resulting gelled hydrocarbon had a 95 second funnel time at 75° F., a viscosity of 45 centipoise at 75° F. and a viscosity of 195 centipoise at 250° F.

EXAMPLES 4 through 10

The procedure of Example 1 was repeated with the variations in hexanol content, geller to hydrocarbon concentration and TEP to P$_2$O$_5$ ratio indicated in the following table:

| Example No. | Hexanol Content (Moles)-(wt. %) | Geller Conc. | TEP:P$_2$O$_5$ Ratio |
|---|---|---|---|
| 4 | 0.37–13.0 | 8gpt | 1.32:1 |
| 5 | 0.75–23.0 | 8gpt | 1.32:1 |
| 6 | 1.50–44.5 | 8gpt | 1.32:1 |
| 7 | 1.50–44.5 | 8gpt | 1.15:1 |
| 8 | 1.50–44.5 | 8gpt | 1.0:1.0 |
| 9 | 2.62–84.3 | 8gpt | 1.0:1.0 |
| 10 | 2.81–91.5 | 8gpt | 1.0:1.0 |

The resulting gelled hydrocarbons had the following funnel times and viscosities:

| Example No. | Funnel Time/ Viscosity (sec./cp.)* |
|---|---|
| 4 | 41/45 |
| 5 | 39/42 |
| 6 | 34/42 |
| 7 | 238/60 |
| 8 | 196/66 |
| 9 | 143/60 |
| 10 | 85/51 |

*75° F.; 170 reciprocal seconds shear rate; measured at 24 hours aging time, except for example 10 which was measured at 2 hours.

The foregoing disclosure and examples are illustrative only. As will be apparent to those skilled in the art, various changes may be made in the ingredients, molar quantities, cure times, etc., within the scope of the appended claims, without departing from the spirit of the invention.

What is claimed is:

1. A hydrocarbon gelling agent comprising the reaction product of (1) a polyphosphate intermediate produced by reacting triethyl phosphate and phosphorous pentoxide and (2) a mixed alcohol comprising from about 13% to about 92% by weight hexanol.

2. A hydrocarbon gelling agent according to claim 1 wherein said mixed alcohol comprises a mixture of alkyl alcohols having 6 to 10 carbons in their alkyl groups.

3. The hydrocarbon gelling agent according to claim 1 wherein from about 1.0 to about 1.3 moles of triethyl phosphate are provided for each mole of phosphorous pentoxide.

4. The hydrocarbon gelling agent according to claim 1 wherein approximately 3.0 moles of total mixed alcohol are provided for each mole of phosphorous pentoxide.

5. The hydrocarbon gelling agent according to claim 1 wherein said mixed alcohol comprises approximately 23% by weight hexanol.

6. A hydrocarbon gelling agent comprising the reaction product of (1) a polyphosphate intermediate produced by reacting approximately 1.3 moles of triethyl phosphate and approximately 1.0 moles of phosphorous pentoxide and (2) approximately 3.0 moles of a mixed alkyl alcohol, said alcohol comprising approximately 23% by weight hexanol.

* * * * *

UNITED STATES PATENT AND TRADEMARK OFFICE
CERTIFICATE OF CORRECTION

PATENT NO. : 4,877,894
DATED : October 31, 1989
INVENTOR(S) : David A. Huddleston It is certified that error appears in the above—identified patent and that said Letters Patent is hereby corrected as shown below:

Column 2, line 16, delete "rresent" and replace with -- present --.

Column 5, line 10, delete "lineasr" and replace with -- linear --.

Signed and Sealed this

Twenty-first Day of May, 1991

*Attest:*

HARRY F. MANBECK, JR.

*Attesting Officer*      *Commissioner of Patents and Trademarks*